United States Patent [19]

Schrier

[11] Patent Number: 4,611,893
[45] Date of Patent: Sep. 16, 1986

[54] EYE CHART FOR SCREENING COMPUTER MONITOR OPERATORS

[75] Inventor: Melvin Schrier, Tenafly, N.J.

[73] Assignee: Eyedex Associates, Fort Lee, N.J.

[21] Appl. No.: 641,036

[22] Filed: Aug. 14, 1984

[51] Int. Cl.[4] .............................................. A61B 3/02
[52] U.S. Cl. ................................................... 351/239
[58] Field of Search ................ 351/239, 240, 241, 242

[56] References Cited

U.S. PATENT DOCUMENTS 1,747,844  2/1930  Ritholz ............................ 351/239 X
3,844,641 10/1974  Nowak ............................. 351/240 X Primary Examiner—Rodney B. Bovernick
Attorney, Agent, or Firm—Aaron B. Karas

[57] ABSTRACT

The present invention relates to a novel visual acuity chart for testing operators of computers and other apparatus employing cathode ray tube monitors for potential vision problems.

1 Claim, 1 Drawing Figure

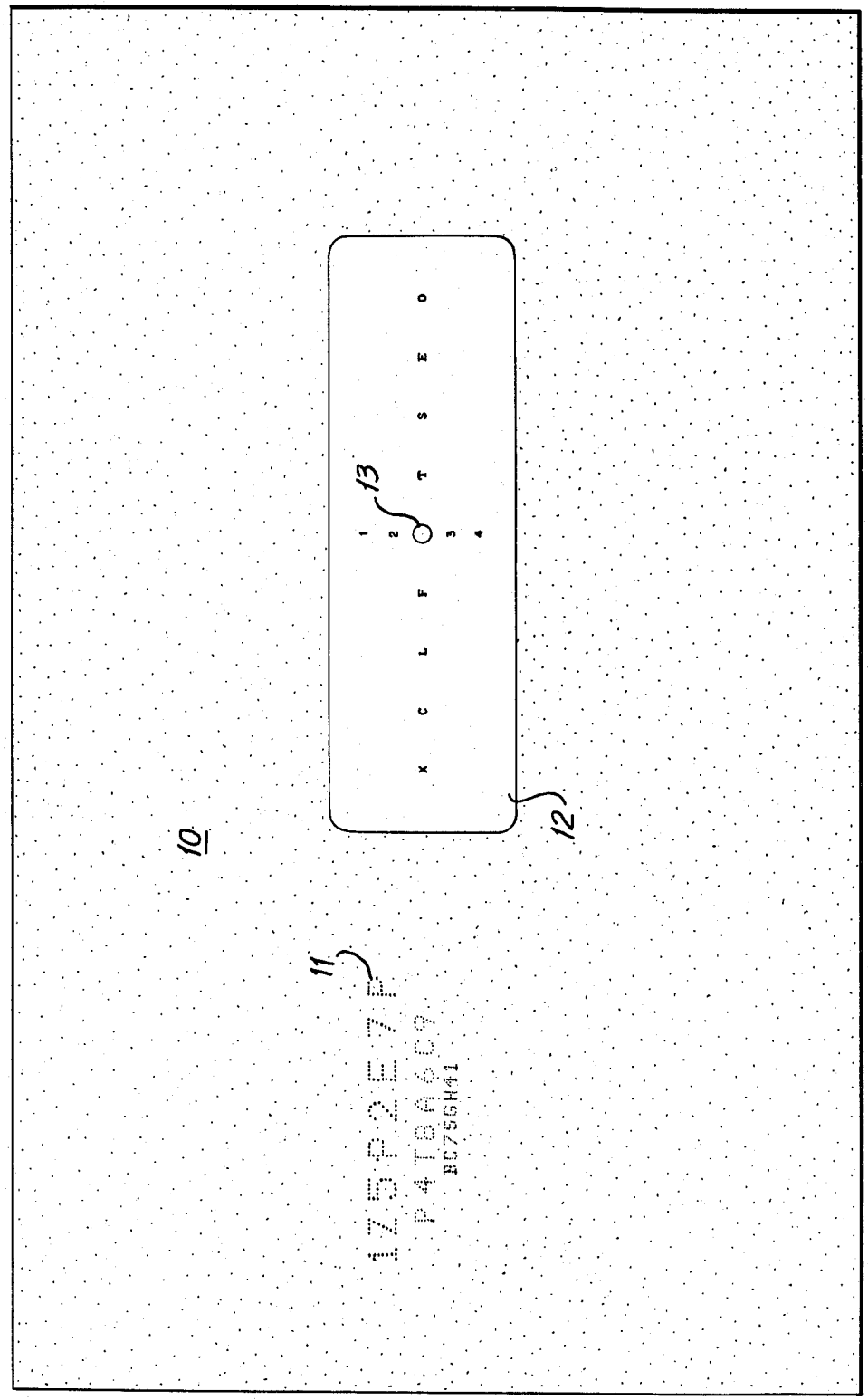

EYE CHART FOR SCREENING COMPUTER MONITOR OPERATORS

In the past five years the use of cathode ray tubes has proliferated as a result of the growth of personal computers and word processors. Operators of such equipment which have cathode ray tube monitors spend many continuous hours before the screen.

At present there is no visual acuity screening test or equipment which is capable of specifically testing and quantifying potential vision problems of computer operators.

Various visual acuity test charts have been developed in the prior art for various purposes in an attempt to improve or modify the well known Snellen standard eye testing chart. Typical of such charts are those described in U.S. Pat. Nos. 1,999,054, 2,385,992, 4,257,690, 4,324,459, and 4,365,873.

U.S. Pat. No. 1,999,054 relates to a series of visual acuity characters formulated to produce a uniform visibility by constructing or forming the symbol as a letter, numeral or other suitable character from segments or parts of the same geometrical figures such as circles and rectangles. U.S. Pat. No. 2,385,992 discloses an improvement on the Snellen chart using a series of targets comprising geometric figures such as squares in a checkerboard pattern.

U.S. Pat. No. 4,257,690 is yet another improvement variation on the Snellen test with the intent and purpose to improve recognition of letters during testing. The eye chart has a plurality of rows of letters where each letter is composed of a line stroke having a plurality of adjoining black and white segments to provide an average reflectance which is the same as the reflectance of the grey background of the chart.

U.S. Pat. No. 4,324,459 discloses an optical test pattern for testing the quality of optical elements and/or optical paths between such elements by use of an arrangement of separated and narrow, uniform optical density wedges, wherein different wedges of the arrangment have different densities.

U.S. Pat. No. 4,365,873 discloses an improvement on the Snellen chart which recognizes that the stimulus response of a visual system is analogous to a filter function. A chart is described which relies on a series of patches on a chart and their interrelationship to achieve the desired improved results in measuring.

While the prior art, typified by the foregoing references has described a number of improvements for testing visual acuity, little if any thought has been given to a relatively new phenomena and the visual problems created by its use. The phenomenal growth of computer usage, and particularly smaller computers of the personal or desk top type employing a cathode ray tube monitor generally having a screen dimension of twelve inches or less has created a large group of persons potentially susceptible to eye stress of various kinds. While occasional use of such computer terminal monitors seldom creates problems, regular use of such computers for extended periods of time does tend to create problems.

It is an object of this invention to provide a thorough, rapid, simple and inexpensive method for testing users of computer equipment to anticipate or determine by simple testing whether a subject is experiencing unusual visual difficulties from use of computer monitors.

The invention comprises providing a series of letters and numerals in what is referred to in the computer industry as dot matrix form, i.e., a series of alternating dots and spaces instead of solid lines to form the letters and numerals.

Although the present invention may be satisfactorily used with conventional eye charts or other similar test devices, it is most emminently suited for use on eye charts such as used in the vision screening kit described in my U.S. Pat. No. 4,279,479. By use of this device the patient can be tested in a fashion similar to the way the subject would be seated and working before a computer monitor at a normal distance of two feet. If desired, the size of the characters can be reduced or enlarged and different eye charts employed, depending on whether the user works with a six inch, nine inch or twelve inch monitor at the normal working distance of twenty four inches.

Other and further objects and advantages of the present invention will be hereinafter described and the novel features thereof defined in the appended claims, taken in connection with the appended drawings, in which eyechart 10 has located thereon a series of rows of letters and numerals 11 in dot matrix form, the size of the letters and numerals and the distance between the rows being determined by the distance at which the testing is being conducted. In addition, for full testing for phoria as well as visual acuity, the eyechart may also contain, adjacent to the dot matrix letters and numerals 11, a phoria testing pattern 12 and a lamp opening 13 thereby enabling the operator to expand the use of the eyechart and provide a more comprehensive examination, when employed with vision testing kits.

In use, the chart will preferably be employed at a distance of two feet the eyes from to more closely duplicate actual use conditions the patient would experience. In such cases, when testing operators of computers having twelve inch monitors, the 20/140 letters would have a height of 6 mm., the 20/100 letters a height of 4.5 mm and the 20/60 letters a height of 3 mm. Of course, it is to be understood that by changing letter size, other distances may be employed in testing the patient or users of different dimension monitor likewise screened.

A most suitable means for using the eyechart of the present invention in testing for potential problems which computer operators may experience is to use the eyechart in a vision testing kit such as that described in my U.S. Pat. No. 4,279,479. The eyechart of the present invention can be easily substituted for the eyechart described in said patent and the subject then screened at a predetermined distance for all of the tests for which the vision screening kit is employed as well as for potential computer monitor use related problems.

By scaling the right side letters 12 which form the phoria test pattern and are based on the conventional Snellen configuration, so they can be employed at two feet instead of the ten foot test distance described in U.S. Pat. No. 4,279,479, all necessary visual testing can be carried out for operators of computer monitors.

What is claimed is:

1. An eye testing chart employing means for screening for and quantifying the visual acuity of operators of computer monitors and screening for visual acuity, lateral phoria and vertical phoria, comprising in combination a first part comprising three rows of letters and numbers of predetermined size and spacing in dot matrix configuration suitable for use at a predetermined testing distance of about two feet wherein the top row of said rows of letters and numbers employs letters 6.0 mm. high, the center row of said row of letters and numbers employs letters 4.5 mm. high and the bottom row of said rows of letters and numbers employs letters 3.0 mm. high and a second part comprising an intersecting vertical and horizontal row of equal sized letters and numbers, 1 mm. in height, spaced 2 prism diopters apart.

* * * * *